United States Patent
Skerl (10) Patent No.: US 9,907,977 B2
(45) Date of Patent: Mar. 6, 2018

(54) CROSS-LINKING OF EYE TISSUE

(71) Applicant: Novartis AG, Basel (CH)

(72) Inventor: Katrin Skerl, Erlangen (DE)

(73) Assignee: Novartis AG, Basel (CH)

( * ) Notice: Subject to any disclaimer, the term of this patent is extended or adjusted under 35 U.S.C. 154(b) by 72 days.

(21) Appl. No.: 14/711,640

(22) Filed: May 13, 2015

(65) Prior Publication Data

US 2016/0059032 A1 Mar. 3, 2016

(30) Foreign Application Priority Data

Aug. 26, 2014 (DE) .................. 10 2014 012 675

(51) Int. Cl.
| | | |
|---|---|---|
| *A61B 18/18* | (2006.01) | |
| *A61N 5/06* | (2006.01) | |
| *A61F 9/008* | (2006.01) | |
| *A61F 9/00* | (2006.01) | |

(52) U.S. Cl.
CPC .............. *A61N 5/062* (2013.01); *A61F 9/008* (2013.01); *A61F 9/0008* (2013.01); *A61F 2009/00853* (2013.01); *A61F 2009/00872* (2013.01); *A61F 2009/00878* (2013.01)

(58) Field of Classification Search
CPC ............ A61N 5/062; A61N 2005/0661; A61F 2009/00872; A61K 31/525
USPC ........ 604/20, 294, 521; 606/4–6; 607/88–94
See application file for complete search history.

(56) References Cited

U.S. PATENT DOCUMENTS

| | | | | |
|---|---|---|---|---|
| 6,530,944 B2* | 3/2003 | West | .................. | A61K 41/0052 424/497 |
| 2002/0187935 A1* | 12/2002 | Redmond | ............... | A61F 9/008 514/100 |
| 2008/0015315 A1* | 1/2008 | Chang | .................. | C08F 220/56 525/326.9 |
| 2008/0045865 A1* | 2/2008 | Kislev | .................... | A61B 5/411 601/3 |
| 2010/0114109 A1* | 5/2010 | Peyman | .................. | A61F 7/007 606/107 |
| 2010/0210996 A1* | 8/2010 | Peyman | .................. | A61F 7/007 604/20 |
| 2011/0052672 A1* | 3/2011 | Krishnan | ........... | A61K 41/0052 424/450 |
| 2011/0282333 A1* | 11/2011 | Herekar | ............. | A61F 9/00821 606/5 |
| 2011/0306956 A1* | 12/2011 | Islam | ..................... | A61B 18/20 606/15 |
| 2012/0220991 A1* | 8/2012 | Jenny | .................... | A61B 18/20 606/3 |

(Continued)

FOREIGN PATENT DOCUMENTS

| | | |
|---|---|---|
| WO | 2011152861 A2 | 12/2011 |
| WO | 2012135073 A2 | 10/2012 |

OTHER PUBLICATIONS

Deane, Nanodiamond-embedded contact lenses may improve glaucoma treatment, Science + Technology, UCLA, Feb. 13, 2014.

(Continued)

*Primary Examiner* — John R Downey (57) ABSTRACT

The present disclosure relates to the cross-linking of eye tissue. Embodiments of the disclosure relate to the activation of a photosensitizer and/or nanoparticles for the cross-linking of eye tissue.

7 Claims, 4 Drawing Sheets

(56) References Cited

U.S. PATENT DOCUMENTS

| | | | | |
|---|---|---|---|---|
| 2012/0296321 | A1* | 11/2012 | Frey | A61F 9/00827 606/5 |
| 2013/0310728 | A1* | 11/2013 | Seiler | A61N 5/062 604/20 |
| 2014/0005379 | A1* | 1/2014 | Gu | A61K 47/26 536/112 |
| 2016/0151202 | A1* | 6/2016 | Scarcelli | A61F 9/008 606/5 |

OTHER PUBLICATIONS

Rossi et al, Laser Activated Gold Nanorods for the Photothermal Treatment of Cancer, Excerpt from the Proceedings of the 2012 Comsol Conference in Milan.

Tachibana, Characterization of Laser-Induced Defects and Modification in Carbon Nanotubes by Raman Spectroscopy, Physical and Chemical Properties of Carbon, 2013, Nanotubes, pp. 31-52.

Yamakoshi et al, Active Oxygen Species Generated from Photoexcited Fullerene (C60) as Potential Medicines: O2—versus 1O2, J. Am. Chem. Soc. 2003, 125, pp. 12803-12809.

Sengupta et al, Efficient Intracellular Delivery of Molecules with High Cell Viability Using Nanosecond-Pulsed Laser-Activated Carbon Nanoparticles, ACS Nano, 2014, vol. 8, No. 3, pp. 2889-2899.

Donaldson et al, The Pulmonary Toxicology of Ultrafine Particles, Journal of Aerosol Medicine, vol. 15, No. 2, 2002, pp. 213-220.

Donaldson et al, Nanotoxicology, Occup Environ Med, 2004, 61, pp. 727-728.

Oberdorster et al, Nanotoxicology: An Emerging Discipline Evolving from Studies of Ultrafine Particles, Environmental Health Perspectives, Jul. 2005, vol. 113, No. 7, pp. 823-839.

De Jong et al, Drug delivery and nanoparticles: Applications and hazards, Internal Journal of Nanomedicine, 2008, 3 (2), pp. 133-149.

Borm et al, The potential risks of nanomaterials: a review carried out for ECETOC, Particle and Fibre Toxicology, 2006, 3, 11.

Sengupta et al, Laser-Activated Carbon Nanoparticle Cellular Damage and Prevention, Pharmaceutical Discovery, Development and Manufacturing Forum, AIChE Annual Meeting, Nov. 7, 2013.

Chakravarty et al, Delivery of molecules into cells using carbon nanoparticles activated by femtosecond laser pulses, Nature Nanotechnology, Jul. 18, 2010, pp. 607-611, 2010 Macmillan Publishers Limited.

* cited by examiner

CROSS-LINKING OF EYE TISSUE

TECHNICAL FIELD

The present disclosure relates to the cross-linking of eye tissue. Embodiments of the disclosure relate to the activation of a photosensitizer and/or nanoparticles for the cross-linking of eye tissue.

BACKGROUND

In the field of ophthalmology it is known to utilize a so-called photosensitizer and electromagnetic radiation to alter the biomechanical and biochemical properties of eye tissue, namely the cornea, for example, for therapeutic purposes.

The human eye is delimited by the outer coat of the eyeball. In the rear region of the eye, the outer coat of the eye is formed by the white sclerotic coat (sclera). The cornea, which is permeable to visible light, is located in the anterior region. Deformations of the outer coat of the eye can be the cause of defective vision. For example, one form of short-sightedness, axial myopia, can result from a sclerotic axial elongation of the eye. An ellipsoidal surface of the cornea can lead to a form of astigmatism, which is referred to as keratoectasia or astigmia. Keratoconus is a further disease of the cornea. In keratoconus, an unnatural softening of the cornea leads to a progressive thinning and conical deformation of the ocular cornea. As the convexity increases, the cornea usually becomes thinner underneath the center or the highest point (apex) of the cornea. In rare cases, perforations can form in the posterior cornea, thereby allowing the fluid from the anterior chamber of the eye to enter the cornea. This is referred to as acute keratoconus, which must be treated immediately, for example, with the medical procedure known as keratoplasty.

Brillouin spectroscopy was combined with OCT (optical coherence tomography) to create a method for the biomechanical, contactless measurement of the stability of the human cornea in order to detect an early stage of keratoconus, thereby making it possible to intervene at an early stage and prevent the disease from progressing.

A subsequent application can be that of stabilizing the cornea by cross-linking. This treatment results in a photochemical, non-tissue abrading stabilization or alteration of the biomechanical and biochemical properties of the cornea. A photosensitizer solution is applied onto or into the eye tissue to be altered and is exposed to radiation that cures the photosensitizer. Electromagnetic radiation in the wavelength range from approximately 300 nm to approximately 800 nm (UV-A radiation or NIR radiation) is usually used as the primary radiation in this case.

Vitamin B2, which is also known as riboflavin, is commonly used as the photosensitizer at the present time. In original applications, the riboflavin was made viscous by the carrier medium dextran such that the epithelium of the cornea had to be removed, at least in part, in order to ensure that riboflavin penetrated the cornea. Modern compositions of active ingredients are liquid like water and have already overcome the limitations for diffusion of the riboflavin molecules into the tissue of the cornea, and therefore the painful removal of the epithelium—and the resultant pain experienced by the patient and the subsequent healing process of the epithelium—no longer appears necessary.

The objective of corneal cross-linking is that of strengthening the stability of the cornea. The main tissue of the cornea, the so-called stroma, comprises individual collagen fibers, which are connected to one another. The corneal stroma can be treated in a specific manner in order to create additional bonds between the individual collagen fibers, i.e. cross-links. In the specific treatment of the corneal stroma, it is possible, for example, to first remove the superficial protective layer, in particular the tear film, the epithelium, and Bowman's membrane (also referred to as Bowman's layer or anterior limiting lamina) using alcohol or by folding open the flap (a small cover having a hinge-type connection to the tissue) or cap (a small cover without a connection to the tissue), for example in laser in-situ keratomileusis (LASIK), apply the photosensitizer, such as riboflavin, and subsequently irradiate the corneal tissue with UVA light for approximately 30 minutes. The linking (also referred to as cross linkage) is often referred to as cross-linking. The individual fibers therefore form a "denser mesh" with one another, which increases the overall stability of the cornea.

Conventional methods for preparing an eye for the introduction of photosensitizer into the eye tissue comprise a source for laser radiation, means for guiding and focussing the laser radiation relative to the eye tissue, and a computer for controlling the aforementioned means. The computer is programmed to control the laser radiation such that the laser radiation creates at least one channel in the eye tissue that extends at least partially in the interior of the eye tissue, e.g., from the surface of the eye tissue into the interior thereof. It is therefore possible to easily introduce the photosensitizer into at least one channel in a targeted manner without the need to remove considerable portions of the epithelium for this purpose or, for example, to fold open a flap or remove a cap.

SUMMARY

According to the present disclosure, the cross-linking of eye tissue takes place in a manner that is more targeted and is faster for the patient, thereby ensuring that the patient does not have to wait for 20 to 30 minutes. In addition, the disclosure supports the treatment procedure and the patient's comfort, since the patient is subjected to an eyelid retractor for a shorter period of time, for instance.

According to a first aspect, a device for the cross-linking of eye tissue is provided. The device comprises an instrument designed to introduce or apply a photosensitizer and nanoparticles into or onto the eye tissue. The device further comprises a light source designed to activate the photosensitizer, which has been introduced or applied, and/or the nanoparticles, which have been introduced or applied, for the cross-linking of the eye tissue.

The eye tissue can be or can comprise corneal tissue, for example. In this case, the cross-linking of the eye tissue is considered to be cross-linking of the cornea. The short curing time can be achieved by adding nanoparticles to the photosensitizer and activating the photosensitizer and/or the nanoparticles.

In the remainder of this application, the term "photosensitizer" will be used in a general sense, wherein this term should not be considered to be a limitation to a certain type and number of "photosensitizers" that are used. In addition, the term "nanoparticles" is used in the remainder of this application, wherein, in one possible embodiment, this term includes biologically degradable nanoparticles. According to the disclosure that is described, it is also possible to use nanoparticles that are non-biologically degradable, but which are non-toxic or have a toxicity that was reduced by appropriate additives.

Any number beginning with just one type of photosensitizer and just one type of nanoparticle is feasible. It is possible, for example, to use one certain type of photosensitizer and one certain type of nanoparticle. It is also possible to use a plurality of different photosensitizers and a plurality of different nanoparticles. The only relevant point is that the cross-linking of the eye tissue is activated, as will be explained in greater detail in the following.

In the case in which the photosensitizer and the nanoparticles are applied onto the eye, both the photosensitizer and the nanoparticles can penetrate the eye tissue via diffusion, for example, in order to be activated there and achieve the desired effect of cross-linking. Nanoparticles can pass through natural obstacles of the body, such as the cornea and tear film, i.e. the nanoparticles can make it easier for the photosensitizer to diffuse into the eye tissue.

The light source can be designed to activate the photosensitizer, the nanoparticles, or the photosensitizers and the nanoparticles. In a first embodiment, the light source can be such a light source or can comprise a light source that is designed to activate only the photosensitizer. Reference is made here to the aforementioned details regarding the cross-linking by the activated photosensitizer. The nanoparticles can be used as a catalyst or catalysts, for example, for the cross-linking by the photosensitizer and can accelerate the cross-linking, for example.

It is possible to use light in the IR, NIR, visible, or UV range for the activation of the photosensitizer. Light in the wavelength range from 190 nm to 500 nm, e.g., 270 nm, 366 nm or 445 nm, can be used to activate the photosensitizer. Riboflavin can be used as the photosensitizer and a UV light source can be used as the light source, for example. The light source can be designed, for example, to provide light in a wavelength range from 360 nm to 370 nm for the cross-linking of the eye tissue, such as the cornea, for example, i.e. in order to generate new protein bonds in the cornea. The wavelength range from 360 nm to 370 nm is absorbed at a maximum level by a human cornea saturated with riboflavin. There are other photosensitizers, however, that can be activated via radiation with light in another wavelength range. The stiffness of the cornea can be improved by a factor of up to 1.5 by corneal cross-linking.

As described above by reference to the wavelength range, the light source can be or comprise a UV light source. As an alternative or in addition, the light source can be or comprise one or more UV-light emitting diodes (LEDs), one or more glass fibers, and/or one or more optical waveguides. It is feasible to provide a plurality of UV LEDs, glass fibers, or optical waveguides as the light source. Any of the plurality of UV LEDs, glass fibers, or optical waveguides can be configured to provide light for the activation of the photosensitizer.

In an alternative embodiment, it is also possible to use a refractive laser, such as an IR-FS laser, a UV-FS laser, an excimer laser or a combination thereof, provided a suitable scattering element is integrated into the optical path and the wavelength appropriate for curing is provided by the scattering element.

In an alternative method for forming a channel in the stroma of the cornea of the eye, the selection of the UV LEDs, glass fibers or optical waveguides permit one or more partial surfaces of the eye tissue to be irradiated with the light, wherein the intention is for only certain regions to be acted upon by the photosensitizer and the nanoparticles. In this manner, the cross-linking can be selectively controlled without an invasive surgical procedure to cut channels. The intensity of the light incident on the tissue can be modified by alternately changing the selection.

In a second embodiment, the light source can be a light source or comprise a light source that is designed to activate only the nanoparticles. The nanoparticles, in turn, can then release the photosensitizer, activate the photosensitizer, or release and activate the photosensitizer, for example.

Tissue cross-linking can be advantageous in a specific embodiment of keratoplasty, e.g., DALK, DESEC, DSAEK, epi-keratoplasty. With regard for the DESEC method, only a certain part of the stroma with Descemet's membrane and the endothelium is replaced by a donor material. In the surgical procedure, a type of balloon is inserted into the anterior chamber of the eye, which applies pressure onto the posterior region of the cornea until the donor material heals with the patient's tissue, thereby ensuring that the cornea does not fall into the anterior chamber. In order to accelerate the process and prevent the need for a complex, subsequent operation in order to remove the balloon, it is provided according to the disclosure to use nanoparticles and photosensitizers in order to achieve tissue cross-linking in a short period of time.

Nanoparticles can also be used that form a type of protective layer around the tissue to be healed, as protection against the fluid in the anterior chamber of the eye, into which the active agent of the photosensitizer can be introduced with different nanoparticles in order to accelerate the healing process and/or avoid the artificial anterior chamber.

In a further possible embodiment of lenticule extraction, in the event that the lenticule is disposed in the central or lower region of the stroma relative to the epithelium, it is possible that, instead of the desired surface deformation of Bowman's membrane and the epithelium for implementing the refractive correction, the unwanted deformation of Descemet's membrane and the endothelium, e.g., with respect to the internal pressure of the eye and/or the anterior chamber of the eye, will occur. This would result in foreseeable refractive corrections, which can be prevented by introducing the active agent of the photosensitizer and nanoparticles into the cavity formed by the lenticule extraction.

After the patient's eye has been acted upon by a patient interface to perform such lenticule incisions, and after the lenticule has been removed and the photosensitizer and the nanoparticles have been introduced, the patient interface can be moved onto the patient's eye once more in order apply a defined pressure onto the epithelium and thereby close the cavity in the stroma from the front side, in particular from the side of the epithelium. An appropriate radiation can be introduced in order to cure the active agent and ensure a reliable connection of the two adjacent surfaces resulting from the removal of the lenticule.

With respect to the activation of nanoparticles for releasing active agents, reference is made to known scientific reports (e.g., P. Chakravarty et al, 2010 see [2] in the bibliographical references). These scientific reports disclose that carbon nanoparticles can be activated by laser pulses, for example, thereby making it easier to provide small molecules, proteins, and DNA in cells.

The light source can be a laser or comprise a laser designed to activate the nanoparticles. The wavelength range of the laser can be in the near infrared (NIR) region. The wavelength of the laser can be in the range from 808 to 980 nm (diode laser). The wavelength of the laser can be approximately 810 nm. The wavelength of the laser can be approximately 1064 nm (Nd:YAG laser).

The nanoparticles can absorb the laser energy and convert this, inter alia, to heat. This energy can be used, in turn, to catalyze or accelerate the cross-linking of the collagen by the photosensitizer.

In a third embodiment, the light source can be a light source or comprise a light source that is designed to activate the photosensitizer and the nanoparticles. To this end, the light source can be designed to provide light in a single wavelength range in which the photosensitizer and the nanoparticles can be activated. As an alternative or in addition, the light source can be designed to provide light in two or more at least partially different wavelength ranges, e.g., by means of suitable crystals such as SHG (Second Harmonic Generation) crystals, THG (Third Harmonic Generation) crystals, or by means of two or more different light sources, in at least one of which the photosensitizer is activated and in at least one other of which the nanoparticles are activated.

If light is provided in a single wavelength range in which the photosensitizer and the nanoparticles can be activated, such a wavelength range can be in the UV range, for example, wherein the nanoparticles can possibly be adapted via surface modification in order to be activated in the UV range. The wavelength range can also be in the NIR range, wherein the nanoparticles can be activated in the above-described manner and, simultaneously, the photosensitizer can be activated via the absorption of heat.

In a further embodiment, the light source for activation can be more than one light source or can comprise more than one light source, one of which activates the photosensitizer and the other of which activates the nanoparticles. Therefore, one UV light source and one IR light source can be used next to one another, for example. The UV light source can activate the photosensitizer, for example, while the IR light source activates the nanoparticles, or vice versa. The activation can take place in succession or simultaneously.

According to one embodiment, a laser can be used with an aforementioned scattering element, wherein, after activation of the photosensitizer by means of diffuse light, for example, and a decoupling of the scattering element, the wavelength of the aforementioned laser is converted into coherent light in order to activate the nanoparticles.

According to a further embodiment, the wavelength of the light source can be separated into two beam paths and adapted accordingly by amplification elements, thereby ensuring that different wavelengths are irradiated simultaneously, e.g., by the use of SHG or THG crystals, in order to simultaneously activate the photosensitizer and the nanoparticles.

According to a further embodiment, two different lasers can be disposed in a housing, for example, wherein these lasers use two separate and/or combined beam channels or partial quantities thereof as common beam channels in order to ensure simultaneous activation of the photosensitizer and nanoparticles.

The device can comprise a cross-linking control system. The cross-linking control system can comprise a control computer that is programmed to automatically control the introduction or application of the photosensitizer and the nanoparticles by appropriate dosing devices. As an alternative or in addition, the control computer can be programmed to control the activation of the photosensitizer and/or the nanoparticles. The cross-linking control system can be used to activate the photosensitizer and/or the nanoparticles.

In the case of corneal cross-linking, the photosensitizer and the nanoparticles can be introduced into the corneal tissue or applied onto the corneal tissue in different ways.

The device can further comprise a system that is designed to create at least one incision in the eye tissue for the introduction of the photosensitizer and/or the nanoparticles. This system can comprise at least one laser radiation source and a system for guiding and focusing the laser radiation relative to the eye tissue. The system can further comprise a computer for controlling the system. The computer can be programmed to control the system and/or the laser radiation such that at least one receiving channel is created in the eye tissue, which extends at least partially into the eye tissue and is connected to at least one opening in the surface of the eye.

A point to be stressed here is that the laser radiation source used to create incisions can be a light source that is different from that described above for activation. It is also possible, however, to use the same light source to create the incision and activate the photosensitizer and/or the nanoparticles.

The at least one incision in the eye tissue for the introduction or application of the photosensitizer and the nanoparticles can be created in different manners. The at least one incision can be or comprise one incision and/or at least one channel incision. The at least one channel incision can be created for the introduction of the photosensitizer and/or the nanoparticles into the cornea. For example, the at least one channel incision can form one or more channels for the introduction of the photosensitizer and/or the nanoparticles. The at least one incision can be created for the application of the photosensitizer onto the cornea. The at least one incision can be created by a laser source that is set to provide laser radiation. Examples of laser sources are an attosecond laser, a femtosecond laser, a nanosecond laser, or a picosecond laser. Such laser sources, such as a femtosecond laser, cut eye tissue by the photodisruption of the tissue with the energy of the laser light, which creates a laser induced optical breakthrough (LIOB), which, in turn, generates cavitation bubbles. In summary, the at least one incision, e.g., comprising at least one incision and/or at least one channel incision, can be created by processing the eye tissue, e.g., the cornea, with laser radiation. The photosensitizer and the nanoparticles can be subsequently introduced into the at least one channel incision and/or applied onto the at least one incision.

As mentioned above, the source of laser radiation for creating the incisions can be different from that of the light source for activating the photosensitizer and/or the nanoparticles. In this case, the first step can be that of creating the at least one incision in the tissue by means of the laser radiation source, and then introducing or applying the photosensitizer and the nanoparticles into or onto the tissue and activating the photosensitizer and/or the nanoparticles by means of at least one second light source, as described above.

It is also possible, however, to use the same light source to create the incision and activate the photosensitizer and/or the nanoparticles. In one embodiment, the source of laser radiation used to create the incisions can also be used to activate the photosensitizer and the nanoparticles.

The laser radiation source can provide laser radiation in a wavelength range of 300 nm-1900 nm, for example a wavelength in the range of 300 nm-650 nm, 650 Nm-1050 nm, 1050 nm-1250 nm or 1100 nm-1900 nm. The same laser radiation could also be used to activate the nanoparticles, and can be in the NIR (e.g., approximately 810 nm or 1064 nm), for example. In this case, the laser radiation source can be used to create the incision and activate the nanoparticles. If a further objective is that of activating the photosensitizer, the emitted wavelength range can be varied or a radiation source having a wavelength adapted to the photosensitizer can be used. It is feasible that the light intensity of the laser radiation source can be reduced after the at least one incision is created. The diminished energy or intensity of the laser radiation can then be below the threshold value up to which incisions are created in the tissue. The intensity, for example, can be set in such a manner by means of a Pockels cell, for example. In this case, the photosensitizer and/or the nanoparticles can be activated with the aid of the laser radiation source. As an alternative, the photosensitizer and/or the nanoparticles can be activated with the aid of another radiation source.

The instrument for introducing or applying the photosensitizer and the nanoparticles can be a cannula or a hollow needle, for example. The instrument for introducing the photosensitizer can be a cannula, through which the photosensitizer can be introduced into the eye tissue. The cannula can comprise two or more outlet openings for introducing the photosensitizer into the eye. In all embodiments, it is also possible to inject a gas, for example air, into the one cannula or the plurality of cannulas. The instrument for applying the photosensitizer and the nanoparticles can be a cannula, hollow needle, pipette, or another type of instrument, for example, that permits precise dosing of the photosensitizer. The instrument for applying the photosensitizer and the nanoparticles is a cannula, for example.

The photosensitizer is suitable for and capable of stabilizing tissue by cross-linking. The photosensitizer can be suitable for and capable of inducing the collagen cross-linking between collagen fibers by the formation of covalent and trivalent cross-links. For corneal cross-linking, the photosensitizer can comprise any suitable ingredients that stabilize the corneal tissue. The photosensitizer can be selected from riboflavin (vitamin B2), lysyl oxidase, transglutaminase, sugar aldehydes, ethylcarbodiimide, glutaraldehyde, formaldehyde, or mixtures thereof, e.g., Karnovsky's solution.

One or more further ophthalmological active agents can be added to the photosensitizer. Such active agents can be, for example, active agents that accelerator or improve the tissue healing or hardening. Antibiotics or other therapeutically active eye drops are feasible.

A combination of nanoparticles and photosensitizer can be used for the cross-linking of the eye tissue.

In one embodiment, nanoparticles can be used that are suitable and capable of catalyzing the cross-linking by the photosensitizer. The catalytic capability is the capability, for example, to accelerate the cross-linking of collagen by a photosensitizer.

The catalytic capability can be the dissipation of heat to the surroundings or the creation of radicals on the surface of the nanoparticles. The catalytic capability does not necessarily have to be interpreted so narrowly that the nanoparticles are not consumed at all by the catalytic reaction. Rather, it is also possible for the nanoparticles themselves to be consumed during the reaction. The catalytic capability can therefore be understood to be the capability to accelerate the curing of the tissue by the photosensitizer in contrast to the use of photosensitizers alone.

The curing can be inspected by means of the diagnostic method, such as the use of Brillouin scattering with OCT (optical coherence tomography) and by a color admixture, which becomes colorless upon sufficient curing of the active agent.

The nanoparticles can be suitable for and capable of catalyzing the cross-linking by the photosensitizer. The nanoparticles can be selected from carbon nanorods, fullerenes, and carbon black nanoparticles. This means the nanoparticles can comprise carbon black nanoparticles, for example, or be formed as carbon black nanoparticles. The nanoparticles can have a size in the range of 1-100 nm. In terms of therapy, factors of nanoparticles to be considered are (i) incorporation and release of active agents, (ii) the stability of formulation and storage life, (iii) biocompatibility, (iv) biodistribution and targeting and (v) functionality.

In one embodiment it is feasible to activate only the nanoparticles. These can then catalyze the cross-linking by a non-activated photosensitizer. The nanoparticles can absorb the laser energy and convert this, inter alia, to heat. This energy can be used, in turn, to catalyze or accelerate the cross-linking of the collagen by the photosensitizer.

In one embodiment it is feasible to activate only the photosensitizer. The nanoparticles can then function as catalysts in the classical sense without the need to be catalyzed themselves.

In one embodiment it is feasible to activate the photosensitizer as well as the nanoparticles. The activation of the nanoparticles can take place after the activation of the photosensitizer or simultaneously therewith.

In one embodiment, the photosensitizer can be bound to the nanoparticles. Both the photosensitizer and the nanoparticles can then be absorbed together by the tissue. The photosensitizer can therefore be introduced into or applied onto the tissue by virtue of being bound to the nanoparticles.

In the case in which the photosensitizer and nanoparticles are applied onto the eye, both the photosensitizer and nanoparticles can penetrate the eye tissue by diffusion, for example, i.e. the diffusion of the photosensitizer into the tissue can be simplified by the nanoparticles, for example.

Energy can be supplied to trigger the nanoparticles to release the active agent in the tissue in a targeted manner. The energy required therefor can be supplied by radiation, as described above.

In one embodiment it is feasible for the photosensitizer to not be bound to the nanoparticles. In this case, the photosensitizer can be introduced into or applied onto the tissue together with the nanoparticles. Energy can be supplied in order to activate the photosensitizer and/or the nanoparticles, as described above, so that the cross-linking of the eye tissue takes place.

The usable nanoparticles can consist of natural materials or derivatives thereof (e.g., chitosan, dextrans, gelatins, alginates, liposomes, starch). Other possibilities include polymers such as dendrimers (branched polymers), polylactic acid (PLA), polycyanoacrylate, polyethylenimine, block copolymers, polycaprolactone, albumin, chitosan, hydrogels, poly(ethylene glycol)/poly($\epsilon$-caprolactone), polyalkylcyanoacrylate composites, poly(D,L-lactic-co-glycolic) acid (=PLGA)).

Dendrimers, due to the specific nature thereof, are suitable for the delivery of active agents. These can be functionalized relatively easily on the surface thereof with specific antibodies or other compounds and, due to the dendritic nature and high branching thereof, permit a high load of active agent.

It is also feasible to use ferrofluids (SPIONS, USPIONS), quantum dots, gold nanoparticles, and magnetic iron oxide.

Gold nanoparticles are used over a wide area, can be synthesized in different forms (rods, quantum dots), are commercially available in different size ranges, and can be easily detected in small concentrations. Cells can absorb gold nanoparticles without cytotoxic effects. Gold nanoparticles can also be modified with PEG and then exhibit further reduced toxicity.

Gold nanorods (GNR) have an average shape and size, and therefore the optical absorption thereof in the NIR range (at approximately 810 nm) is maximized (see F. Rossi et al., 2012; [3] in the bibliographical references). A gold nanorod is typically a cylinder having sizes of 40×10 nm (axis× diameter).

Further nanoparticles can be based on carbon (fullerenes, carbon tubes) or silicon.

Carbon-based nanoparticles are suitable for various reasons. The photodynamic capabilities thereof are known. Carbon-based nanoparticles can comprise carbon nanorods, fullerenes, and carbon black nanoparticles (also referred to as soot nanoparticles).

Carbon nanorods (or carbon nanotubes) are long carbon-based rods that can have one wall or several walls. Nanorods have a height-width ratio of >100, with lengths of a few mm and diameters of 0.7 to 1.5 mm for single-walled carbon nanotubes (SWNT or SWCNT) and 2 to 50 nm for multiwall carbon nanotubes (MWNT or MWCNT). Conventional carbon nanotubes respond, e.g., to wavelengths in the range of 248 nm (KrF laser), 532 nm (Nd:YOV$_4$ laser), 632.8 nm (He—Ne laser) (see M. Tachibana, 2013; [4] in the bibliographical references). Various toxic properties have been described for these particles. All these reports address the biocompatibility of nanoparticles in the application for delivery of active agents, however. Applications on the eye have not been described.

Fullerenes have potential as antimicrobial agents, as has been sufficiently disclosed. After photo-excitation, fullerenes are capable of generating reactive oxygen species (see, for example, Yamakoshi et al., 2003; [5] in the bibliographical references).

Graphite is the basic structure of soot nanoparticles (or carbon black nanoparticles or CB nanoparticles). Graphite is a soft, black metallic shiny material that occurs in natural form and can be artificially produced. Individual carbon black nanoparticles can have an average diameter of 25 nm, although in aggregated form often have an average diameter of up to 200 nm. Carbon black nanoparticles can be activated, e.g., by radiation in the wavelength range of 1064 nm (see A. Sengupta, 2013 and 2014; [6] in the bibliographical references).

The oxide groups on the pore surface have the greatest influence on the physico-chemical properties of the carbon black nanoparticles, such as the catalytic, chemical, and electrical reactivity. Primarily, basic hydroxyl-, acidic carboxyl-, as well as carbonyl-, and lactone-groups form on the surface. In the production of active carbon black, functional oxygen groups having a mass fraction of up to 15% can be introduced.

In one embodiment, the nanoparticles can be selected from carbon nanotubes, fullerenes, and carbon black nanoparticles.

Nanoparticles can be procured from known manufacturers and suppliers. The production of the nanoparticles mentioned here is known to a person skilled in the art and does not need to be described in greater detail here.

Moreover, it is feasible for the nanoparticles to be coated with a coating, for example to prevent agglomeration or improve biocompatibility. Such coatings can include different polymers, such as polyethylene glycol (PEG), poly(vinyl pyrrolidone) (PVP), for example natural polymers such as dextran, chitosan, pullulan, and surface-active agents such as sodium oleate, dodecylamine, etc. (see W. De Jong, P. J A Borm; [8] in the bibliographical references). Nanoparticles provided with ethylene glycol can prevent white blood cells from recognizing the nanoparticles as foreign bodies, thereby enabling the nanoparticles to remain in the blood longer, until these can dock to the active site.

Various sizes are feasible for the nanoparticles. Particles having a mean size in the range of 0.1-200 nm, for example 1-100 nm, can be classified as nanoparticles in this case. Other sizes are feasible for the nanoparticles if the nanoparticles are capable of catalyzing or accelerating the cross-linking by the photosensitizer.

The size of nanoparticles can be determined by means of methods known to a person skilled in the art. One feasible method is dynamic light scattering (DLS). Other measurement methods may also be used, however.

A problem associated with nanoparticles that has been a frequent topic of discussion recently is the potential toxicity thereof. In years past, several scientific articles addressed the toxicity of nanomaterials such as fullerenes, carbon nanorods, and quantum dots and showed that many parameters, including the size and surface, as well as the surface modification, contributed to the toxicity (see W. De Jong, P. J A Borm 2008; [8] in the bibliographical references). The biocompatibility can be modified simply by means of slight changes in the size of the nanoparticles. Reference is made to the coatings described above with respect to the surface modification. There are also large data collections on nanoparticle toxicity, to which a person skilled in the art will refer to select the nanoparticles. Such data collections are disclosed, for example, in Donaldson et al 2002, 2004; Oberdörster et al 2005, Borm et al 2006, see also W. De Jong, P. J A Borm 2008 for a brief summary of such data collections (see [9] to [12] in the bibliographical references).

According to a further aspect, a pharmaceutical composition is provided. The pharmaceutical composition comprises the photosensitizer described herein and the nanoparticles described herein for the cross-linking of eye tissue. The photosensitizer and the nanoparticles can be selected as described above.

As one specific example of the pharmaceutical composition, the pharmaceutical composition can comprise riboflavin and carbon black nanoparticles. In a further embodiment, the pharmaceutical composition can comprise riboflavin and gold nanoparticles.

According to a further aspect, the use of the device and/or the pharmaceutical composition for the treatment of ectasia, for example, keratoconus is provided. This means the device and the pharmaceutical composition can be used for the treatment of ectasia, for example, keratoconus. According to a further aspect, the use of the device and/or the pharmaceutical composition in the treatment of keratoplasty is provided. According to a further aspect, the use of the device and/or the pharmaceutical composition in LASIK, e.g., in the secure fastening of the flap, is provided.

According to a further aspect, a method for the cross-linking of eye tissue is provided. The method comprises the introduction or application of a photosensitizer and nanoparticles into or onto eye tissue and providing light having a wavelength that is suitable for activating the photosensitizer and/or the nanoparticles for the cross-linking of the eye tissue.

DESCRIPTION OF FIG. 1

Figure 1:
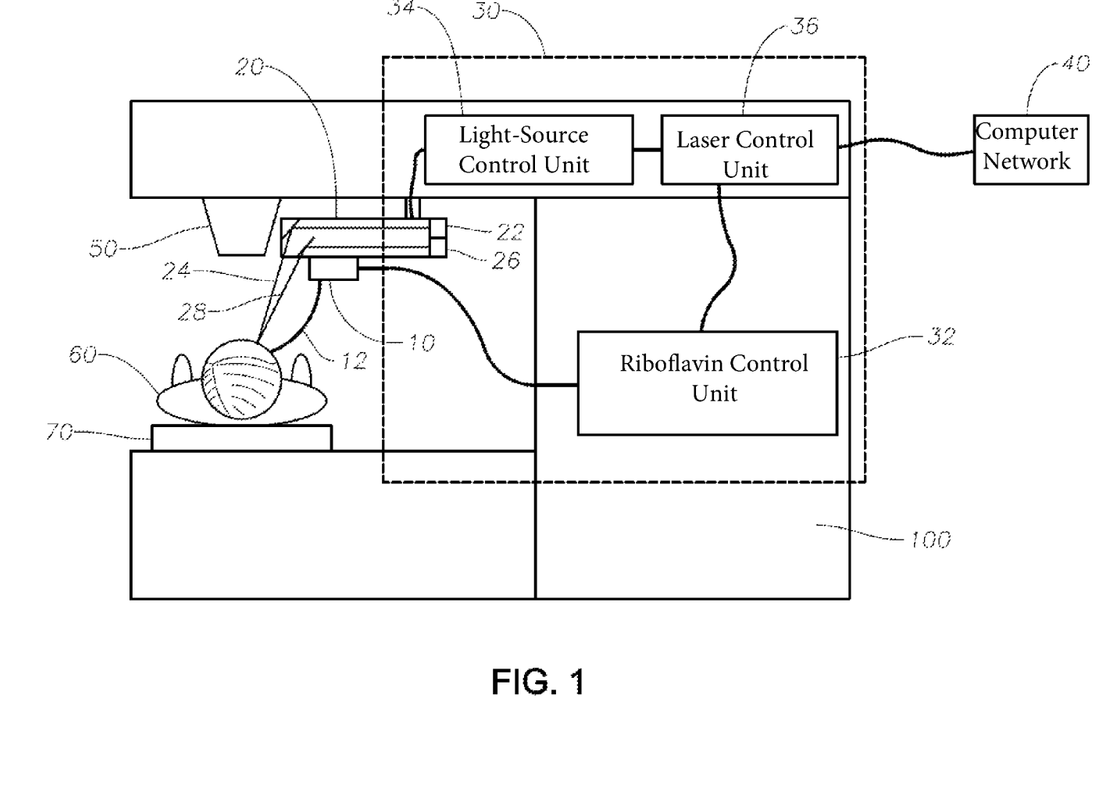
FIG. 1 shows a schematic illustration of an example of a laser system comprising a device for the cross-linking of an eye tissue according to the present invention.

Specific exemplary embodiments will be described in greater detail by reference to the figure that follows. Although individual elements are made more precise therein in order to enhance understanding, this is not intended to limit the subject matter that is shown. For example, the UV light source (22) can also be set to emit light in a different wavelength range.

FIG. 1 shows a schematic illustration of an example of a laser system (100) comprising a device for the cross-linking of eye tissue according to one embodiment. The device comprises a photosensitizer distribution unit (10) designed to introduce or apply a photosensitizer and nanoparticles into or onto the eye tissue. This photosensitizer distribution unit is referred to in the following as a riboflavin distribution unit (10) since, merely for the purpose of clarification and by no means for the purpose of limitation, riboflavin is used in the present example as an example of a photosensitizer and the instrument is configured to provide the photosensitizer and the nanoparticles as well as to dose and distribute the photosensitizers and the nanoparticles. The laser system (100) further comprises an instrument for the application of the photosensitizer and the nanoparticles (12), which can be a cannula, for example. The instrument for applying the photosensitizer and the nanoparticles (12) can be part of the riboflavin distribution unit (10) or can be a unit separate therefrom.

The laser system further comprises a light source (20). In the present example, the light source (20) comprises, for example, a UV light source (22) configured to provide light in the UV wavelength range (24). The light source (20) further comprises, for example, an IR light source (26) configured to provide light in the IR wavelength range (28).

In this case, the laser system (100) further comprises a control computer (30), which, in turn, has separate control units, namely a riboflavin control unit (32), a light-source control unit (34), and a laser control unit (36). The riboflavin control unit (32) is configured to control the riboflavin distribution unit (10) and/or the instrument for applying the photosensitizer and the nanoparticles (12). The light-source control unit (34) is configured to control the light source (20). For example, the light-source control unit (34) can be configured to control the UV light source (22) and the IR light source (26) independently of one another. The laser control unit (36) is configured to control a laser source (50) that provides laser radiation.

Although the UV light source (22) and the laser source (50) are shown as separate units that provide radiation having different properties, it is also possible to provide only one source of radiation that is configured to provide suitable radiation. The radiation can be controlled such that the radiation is suitable for creating at least one incision for the introduction or application of the photosensitizer and the nanoparticles into or onto the tissue and activating the photosensitizer and/or the nanoparticles for the corneal cross-linking.

In the example shown in FIG. 1, the control computer (30) is connected to a computer network, which is referred to herein as WaveNet™ (40). This provides, inter alia, access to patient data and treatment and diagnostic parameters.

FIG. 1 also shows the patient (60) to be treated disposed on a bench (70) of the laser system (100).

A plurality of examples will be outlined in the following to illustrate which effects can be achieved by the use of certain nanoparticles in combination with radiation of various wavelengths. The device shown in FIG. 1, or a similarly designed device, can be used to implement these examples.

Example 1

Figure 2:
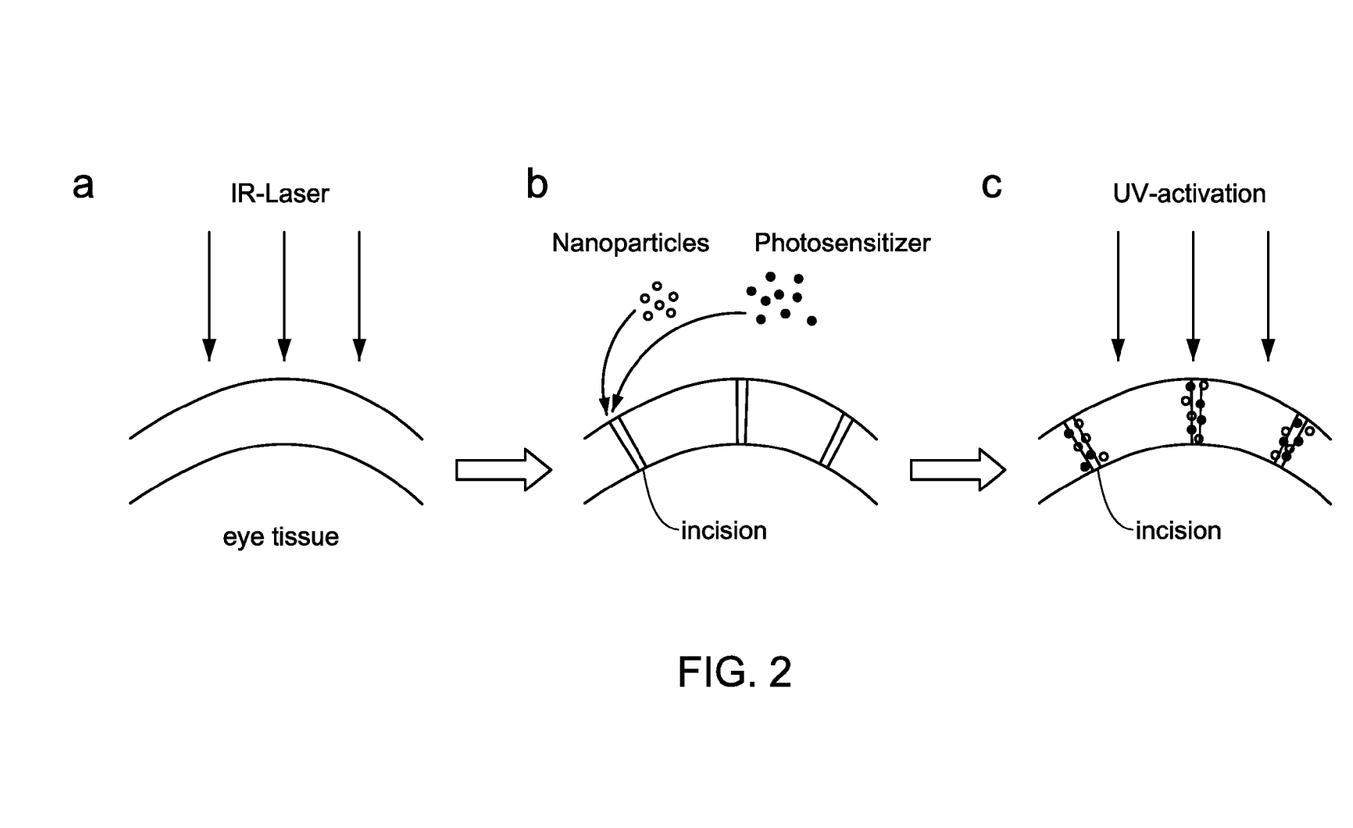
FIG. 2 shows a way of carrying out a cross-linking reaction of eye tissue with photosensitizer and nanoparticles activated by UV-irradiation.

An incision is created in the eye tissue by IR laser radiation (FIG. 2a). Riboflavin and carbon black nanoparticles are introduced into the incision (FIG. 2b). The riboflavin absorbed by the eye tissue and the nanoparticles are then activated by UV radiation in the range of 360 nm to 370 nm (FIG. 2c). The curing time is substantially shortened compared to the application of riboflavin only, without nanoparticles.

Example 2

Figure 3:
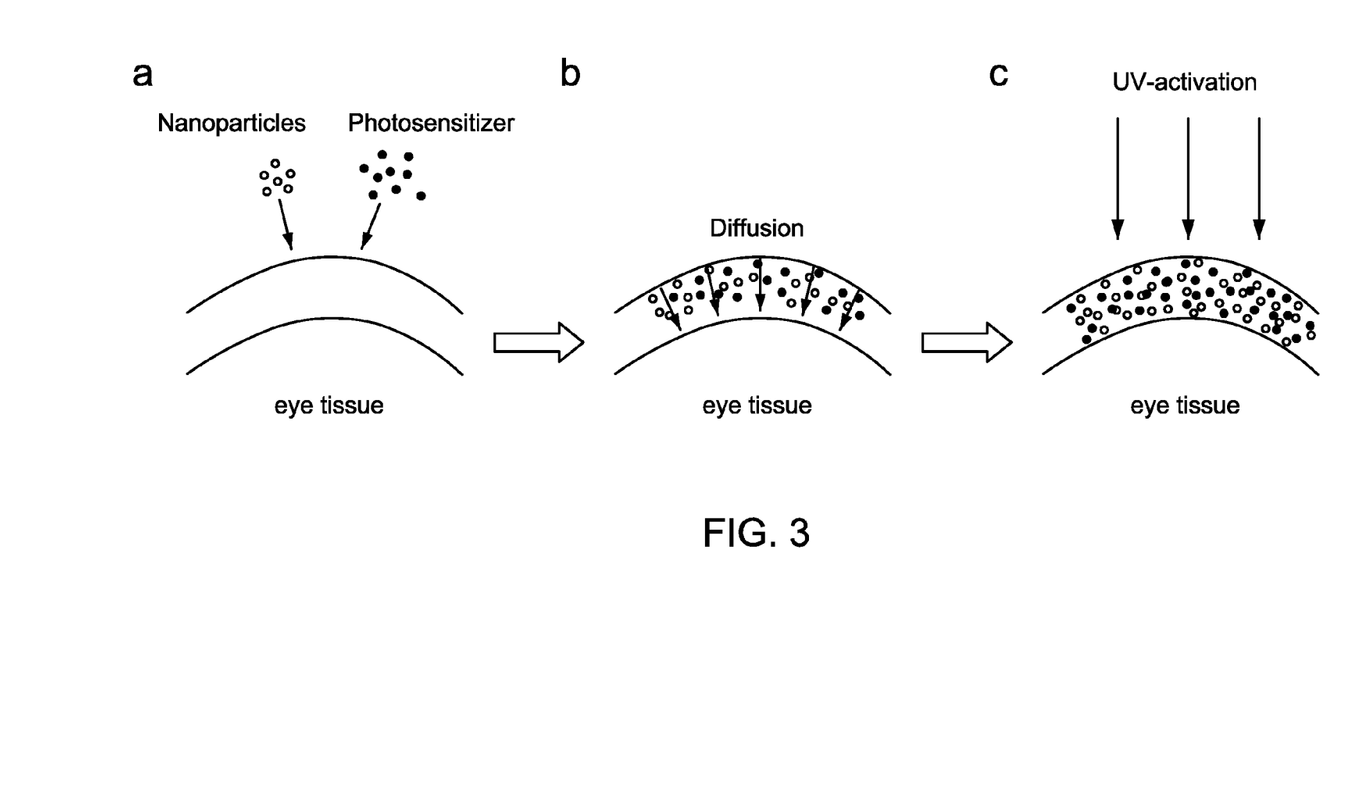
FIG. 3 shows another way of carrying out a cross-linking reaction of eye tissue with photosensitizer and nanoparticles activated by UV-irradiation.

Riboflavin and carbon black nanoparticles are applied onto the eye tissue (FIG. 3a). After a waiting time, the riboflavin and the nanoparticles diffuse into the tissue (FIG. 3b). The riboflavin absorbed by the eye tissue and the nanoparticles are then activated by UV radiation in the range of 360 nm to 370 nm (FIG. 3c). The curing time is substantially shortened compared to the application of riboflavin only, without nanoparticles.

Example 3

Figure 4:
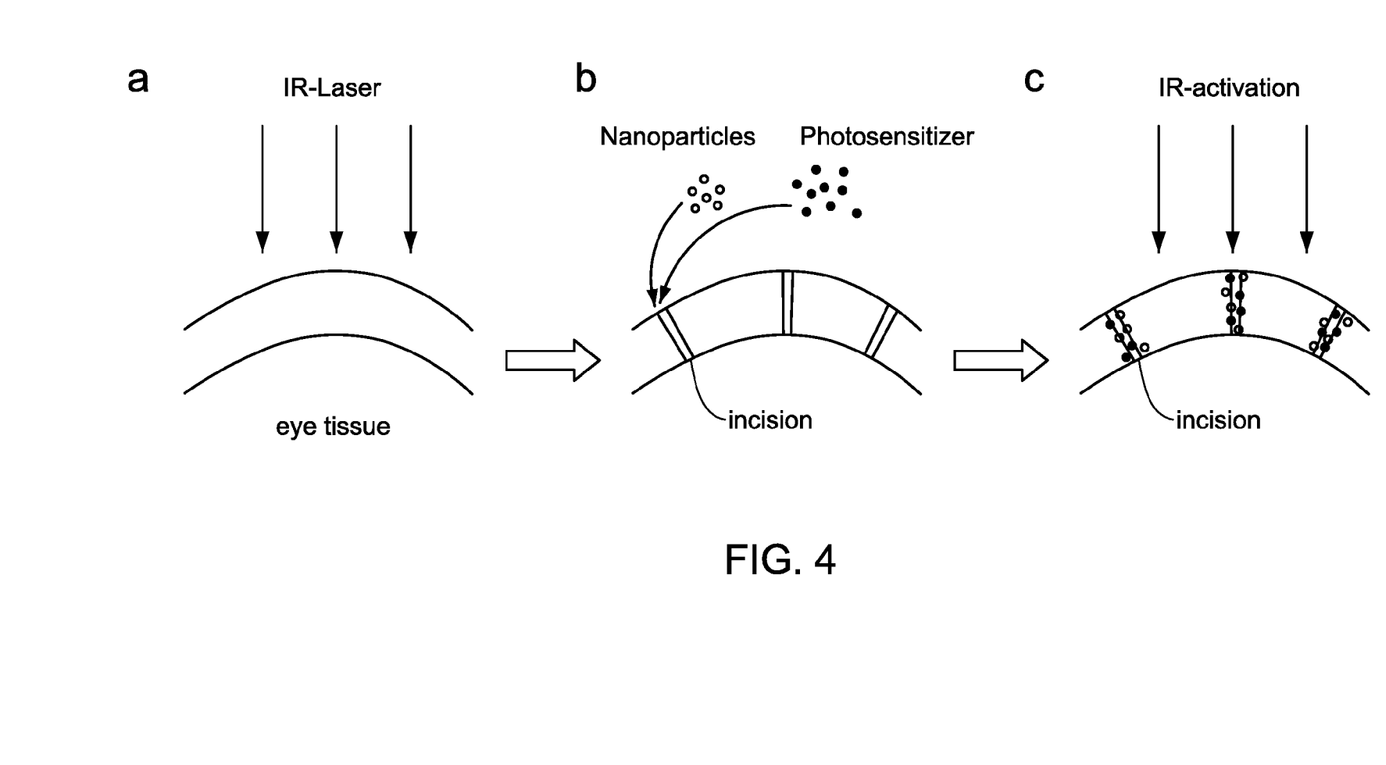
FIG. 4 shows another way of carrying out a cross-linking reaction of eye tissue with photosensitizer and nanoparticles activated by IR-irradiation.

An incision is created in the eye tissue by IR laser radiation (FIG. 4a). Riboflavin and carbon black nanoparticles are introduced into the incision (FIG. 4b). The riboflavin absorbed by the eye tissue and the nanoparticles are then activated by IR radiation in the range of 1064 nm (FIG. 4c). The curing time is substantially shortened compared to the application of riboflavin only, without nanoparticles.

REFERENCES

[1] Brianna Deane, Nanodiamond-embedded contact lenses improve glaucoma treatment, Science and Technology, UCLA, 13 Feb. 2014.
[2] P. Chakravarty et al, Delivery of molecules into cells using carbon nanoparticles activated by femtosecond laser pulses, Nature Nanotechnology, 5, 607-611, (2010).
[3] F. Rossi et al., Laser Activated Gold Nanorods for the Photothermal Treatment of Cancer, Excerpt from the Proceedings of the 2012 Comsol Conference in Milan.
[4] M. Tachibana, Characterization of Laser-Induced Defects and Modification in Carbon Nanotubes by Raman Spectroscopy, Physical and Chemical Properties of Carbon, 2013, Nanotubes, http://dx.doi.org/10.5772/52091.
[5] Yamakoshi et al., Active oxygen species generated from photo-excited fullerene (C-60) as potential medicines: $O_2^-$ versus $^1O_2$. J. Am. Chem. Soc. 2003, 125, 12803-9.
[6] A. Sengupta, Laser-Activated Carbon Nanoparticle Cellular Damage and Prevention, Pharmaceutical Discovery, Development and Manufacturing Forum, AIChE Annual Meeting, 7 Nov. 2013.
[7] A. Sengupta, Efficient intracellular delivery of molecules with high cell viability using nanosecond-pulsed laser-activated carbon nanoparticles, ACS Nano. 2014 March 25; 8(3):2889-99. doi: 10.1021/nn500100x.

[8] W. De Jong, P. J A Borm, Drug delivery and nanoparticles: Applications and Hazards, Int. J. Nanomdedicine, June 2008, 3(2), 133-149.

[9] Donaldson et al., The pulmonary toxicology of ultrafine particles, J. Aerosol. Med. 2002, 15, 213-20.

[10] Donaldson et al., Nanotoxicology, Occup. Environ. Med. 2005, 61, 727-28.

[11] Oberdörster et al., Nanotoxicolgy: An emerging discipline evolving from studies of ultrafine particles, Einvorn Health erspect., 2005, 113, 823-39.

[12] Borm et al 2006, The Potential risks of nanomaterials: a review carried out for ECETOC, PArt. Fiber Toxicol., 2006, 3, 11.

The invention claimed is:

1. A device for the cross-linking of eye tissue comprising:
an instrument designed to introduce a photosensitizer and nanoparticles into the eye tissue, and
a laser radiation source configured to emit radiation that is designed to simultaneously activate each of the photosensitizer and the nanoparticles, the laser radiation source also comprising one or more of a Second Harmonic Generation crystal and a Third Harmonic Generation crystal for generating radiation designed to create a channel through an epithelium layer of the eye tissue;
a system for guiding and focusing the laser radiation relative to the eye tissue, and
a computer for controlling the system, wherein the computer is programmed to control the laser radiation to:
first, create at least one channel at least partially through an epithelium layer of the eye tissue,
second, cause the instrument to introduce the photosensitizer and the nanoparticles into the at least one channel through the epithelium layer of the eye tissue, and
third, simultaneously activate each of the photosensitizer and the nanoparticles, wherein the photosensitizer, when activated, achieves cross-linking in the eye tissue, and wherein the nanoparticles, when activated, catalyze cross-linking by the photosensitizer.

2. The device according to claim 1, wherein the laser radiation source is configured to emit UV light.

3. The device according to claim 1, wherein the laser radiation source is designed to provide light in the wavelength range of 300-1900 nanometers (nm).

4. The device according claim 1, wherein the photosensitizer is selected from a group consisting of riboflavin (vitamin B2), lysyl oxidase, transglutaminase, sugar aldehydes, ethylcarbodiimide, glutaraldehyde, formaldehyde, and mixtures thereof.

5. The device according to claim 1, wherein the nanoparticles are selected from a group consisting of carbon nanorods, fullerenes, and carbon black nanoparticles.

6. The device according to claim 5, wherein the nanoparticles have a size in the range of 1-100 nm.

7. A method of cross-linking eye tissue comprising:
creating at least one channel through an epithelium layer of the eye tissue using a laser radiation source configured to emit radiation that is designed to simultaneously activate each of a photosensitizer and a nanoparticles, the laser radiation source also comprising one or more of a Second Harmonic Generation crystal and a Third Harmonic Generation crystal for generating radiation designed to create the at least one channel through the epithelium layer of the eye tissue;
introducing the photosensitizer and the nanoparticles through the at least one channel through an epithelium layer of the eye tissue and into the cornea; and
simultaneously activating both the photosensitizer and the nanoparticles, wherein the photosensitizer, when activated, achieves cross-linking in the eye tissue, and wherein the nanoparticles, when activated, catalyze cross-linking by the photosensitizer.

* * * * *